US011110057B2

(12) United States Patent
Marcello et al.

(10) Patent No.: US 11,110,057 B2
(45) Date of Patent: Sep. 7, 2021

(54) MICRO PARTICLES FOR ORAL DELIVERY IN ANIMALS

(75) Inventors: Arduini Marcello, Cavriago (IT); Arduini Lauro, Cavriago (IT)

(73) Assignee: KEMIN INDUSTRIES, INC., Des Moines, IA (US)

( * ) Notice: Subject to any disclaimer, the term of this patent is extended or adjusted under 35 U.S.C. 154(b) by 96 days.

(21) Appl. No.: 13/081,581

(22) Filed: Apr. 7, 2011

(65) Prior Publication Data

US 2011/0250286 A1 Oct. 13, 2011

Related U.S. Application Data

(60) Provisional application No. 61/321,604, filed on Apr. 7, 2010.

(51) Int. Cl.
*A61K 9/50* (2006.01)
*A61K 31/14* (2006.01)
*A61K 31/198* (2006.01)
*A61K 9/00* (2006.01)
*A61K 47/12* (2006.01)

(52) U.S. Cl.
CPC .......... *A61K 9/0068* (2013.01); *A61K 9/5015* (2013.01); *A61K 31/14* (2013.01); *A61K 31/198* (2013.01); *A61K 47/12* (2013.01)

(58) Field of Classification Search
CPC .............................. A61K 47/12; A61K 31/198
See application file for complete search history.

(56) References Cited

U.S. PATENT DOCUMENTS

| | | | |
|---|---|---|---|
| 3,451,204 A | 3/1968 | Cramer et al. | |
| 4,533,557 A | 8/1985 | Maruyama et al. | |
| 4,713,245 A | 12/1987 | Ando et al. | |
| 4,832,967 A | 5/1989 | Autant et al. | |
| 4,876,097 A | 10/1989 | Autant et al. | |
| 5,126,151 A * | 6/1992 | Bodor .................. | A23G 4/066 426/305 |
| 5,190,775 A | 3/1993 | Klose | |
| 5,496,571 A | 3/1996 | Blagdon et al. | |
| 5,912,017 A | 6/1999 | Mathiowitz et al. | |
| 6,451,342 B2 * | 9/2002 | Adjei .................. | A61K 9/209 424/468 |
| 7,923,033 B2 | 4/2011 | Cavassini et al. | |
| 2005/0019413 A1 | 6/2005 | Cavassini et al. | |
| 2006/0067984 A1 | 3/2006 | Cavassini et al. | |
| 2007/0202149 A1 | 8/2007 | Faucher et al. | |
| 2007/0244093 A1 | 10/2007 | Boehm et al. | |
| 2007/0292475 A1* | 12/2007 | Campbell ............ | A61K 9/0048 424/428 |
| 2008/0299204 A1 | 12/2008 | Nangia et al. | |
| 2008/0311201 A1 | 12/2008 | Der-Yang et al. | |
| 2012/0141590 A1* | 6/2012 | Malakhov ............ | A61K 9/5089 424/490 |

FOREIGN PATENT DOCUMENTS

| | | |
|---|---|---|
| EP | 0467401 A1 | 1/1992 |
| EP | 0477135 A1 | 3/1992 |
| WO | 2008015203 A2 | 2/2008 |

OTHER PUBLICATIONS

Wikipedia, fatty acids, 4 pages (evidence).*
Wu, Stephen H.W. & Papas, Adreas, Rumen-stable delivery systems, Advanced Drug Delivery Reviews 28 (1997) 323-334.
Deuchler, Kerri N. , Piperovia, Liliana S. and Erdman, Richard A., Milk Choline Secretion as an Indirect Indicator of Postruminal Choline Supply, 1998 J Dairy Sci 81:238-242.
Hartwell, J.R., Cecava, M. J. and Donkin, S. S., Impact of Dietary Rumen Undegradable Protein and Rumen-Protected Choline on Intake, Peripartum Liver Triacylglyceride, Plasma Metabolites and Milk Production in Transition Dairy Cows, 2000 J Dairy Sci 83:2907-2917.
Unkown, "Hydriertes Sojaol, hydrated soya oil", "Europaisches Arzneibuch 7", Jan. 1, 2011, pp. 4396-4397, vol. 7.
Wolfmeier et al., "Waxes", "Ullmann's Encyclopedia of Industrial Chemistry", Jun. 15, 2000, p. 120 vol. 39, Publisher: Wiley-VCH Verlag GmbH & Co. KGaA, Published in: Germany.

* cited by examiner

*Primary Examiner* — Kyle A Purdy
(74) *Attorney, Agent, or Firm* — Nyemaster Goode P.C.

(57) ABSTRACT

A system for the controlled release of one or more physiologically or pharmacologically active substances, comprising compositions in the form of micro particles or granules, particularly for use in the zootechnical and/or veterinary field. The micro particles include a core which contains one or more substances having a pharmacological action, food supplements or diagnostic media, said one or more substances being characterized by the presence, within their chemical structure, of a basic functional group, specifically including an amine functional group. The core comprises also one or more carboxylic acids and/or their salts and eventually one or more excipients. Said core is coated by an outer layer of fats or waxes, and preferably by a mixture of glyceride of fatty acids.

14 Claims, 2 Drawing Sheets

MICRO PARTICLES FOR ORAL DELIVERY IN ANIMALS

This application claims priority to U.S. Patent Application Ser. No. 61/321,604, filed Apr. 7, 2010, which is incorporated herein in its entirety by this reference.

BACKGROUND OF THE INVENTION

The present invention relates generally to compositions in the form of micro particles and, more specifically, to micro particles intended for use in the zootechnical field and/or in the veterinary field.

The oral administration of active substances in the zootechnical field is a problem which is not easy to solve, in particular as regards the possibility to ensure intestinal absorption of adequate doses of said substances, avoiding their massive degradation during passage through the digestive tract of the animal, especially in the case of ruminants.

The aspects of the physiology of the digestive tract of ruminants and of other so-called companion animals or productive livestock are disclosed in detail in many specialist monographs. Among these, some also review the problems linked to the oral administration of active ingredients in such animals, as well as the possible solutions in terms of formulation technology (Development and formulation of veterinary dosage forms 2nd Edition, G. E. Hardee, J. D. Baggot (Edts) Marcell Dekker, New York 1998; S. H. W. Wu, A. Papas, Rumen stable delivery systems, Advanced drug delivery reviews 28 (1997) 323-334). The active ingredients and the supplements of the animal's diet undergo, in the proximal tract of the digestive system, an enzymatic and chemical degradation before reaching the intestinal lumen, which is the site of absorption for said substances. In ruminants, this degradation is particularly substantial due to the presence in the rumen of a microflora which degrades substantially many of the substances which pass through the rumen. One must also consider the slowness with which said substances pass through the rumen. This causes only a small part of the active substances or food supplements to be absorbed by ruminants at the intestinal level, since almost 100% of these molecules is degraded by the microflora of the rumen. Therefore, to allow such substances to be absorbed in the intestine and apply their effectiveness, it is necessary to protect them against degradation at the rumen level. It is in fact known that for example a substance such as choline or its salts are capable of increasing milk production in bovines when they are administered directly at the post-rumen level (S. R. Haretewell et ah, J. Dairy Sci. (2000) 83, 2097-2017 and K. N. Deulcher et al, J. Dairy Sci, (1998) 81, 238-242).

U.S. Pat. No. 4,533,557 discloses the composition of supplements for ruminants in the form of granules or tablets which contain a mixture of biologically active substances, chitosan and protective materials constituted by saturated or unsaturated aliphatic monocarboxylic acids, with a chain having 14 to 22 carbon atoms. The concept behind this invention consists in using hydrophobic substances to build a matrix which is capable of slowing the penetration of biological fluids inside it and consequently of causing a slower release of the substance. The aim is therefore to extend the substance release time by reducing the amount thereof released during rumen transit. Further, the presence of chitosan should provide specific protection against the rumen environment: the pH of the fluid contained in the rumen varies between 5 and 8; chitosan is scarcely soluble in this pH range, but dissolves instead in an acid pH (<5). Therefore, the presence of this type of polymer should give greater integrity to the matrix during rumen holding.

U.S. Pat. No. 5,190,775 discloses the composition of particles or granules for oral administration having a relative density between 0.3 and 2 g/ml, which contain a bioactive substance which is encapsulated by means of a hydrophobic coating which is constituted preferably by hydrogenated vegetable oils coated on their surface with a layer of surfactant in order to prevent its floating within the rumen. In the specific case in which the bioactive substance is choline chloride, it is adsorbed on a vegetable substrate derived from cereals. In another patent, granted to Morgan Manufacturing Co., Inc. (U.S. Pat. No. 5,496,571), a method is disclosed for manufacturing microcapsules which are intended for oral administration and are designed to protect choline chloride against degradation caused by rumen bacteria in order to increase the production of milk in ruminants. These microcapsules contain liquid compositions of choline chloride coated with an outer layer of lipid material selected among hydrogenated and non-hydrogenated animal fats or among hydrogenated vegetable oils.

A series of other patents claims methods and compositions which entail coating a core which contains a bioactive substance by way of materials which are capable of withstanding at least partly rumen degradation and of dissolving and/or degrading in the abomasus or in the distal part of the intestine of ruminants. Among these patents, mention can be made for example of U.S. Pat. Nos. 4,713,245, 3,451,204, and 4,876,097.

U.S. Pat. No. 4,832,967 claims a composition for feeding ruminants which is constituted by a core which contains the bioactive substance, coated by two protective layers. The first of said coatings is a polymeric substance which is capable of forming a film which is stable at pH>5 but is capable of releasing the bioactive substance at pH<3.5. The second coating is a hydrophobic substance. The preparation of multilayer polymeric microspheres for controlled release of drugs, fertilizers, insecticides and chemical indicators is claimed by U.S. Pat. No. 5,912,017, granted to the Massachusetts Institute of Technology.

United States Published Application No. 2005/0019413 describes a composition in the form of particles which contain choline chloride administered in a rumen-protected form. The particles are constituted by a core which consists mainly of choline chloride in the form of crystalline powder, coated by a double protective layer: externally, a continuous layer of carnauba wax and internally a continuous layer of a hydrophobic substance such as hydrogenated soybean oil. Moreover, the core can contain additional substances acting as flow modifiers (silicate, aluminosilicates, zeolites, silica, pearlite) in amounts not exceeding 8% of the weight of the core, and/or acting as binding agents which have a barrier function against moisture (stearates) in an amount equal to 7% of the weight of the core.

United States Published Application No. 2006/0067984 describes compositions in the form of pellets for controlled release of physiologically active substances for zootechnical use. These compositions comprise: i) a core constituted by the physiologically active substance and by a matrix of carnauba wax and/or microcrystalline wax; ii) a first hydrophobic coating layer, which consists of a material which belongs to the category of fats, fatty acids, hydrogenated oils, fatty acid mono- or diglycerides, fatty acid esters or long-chain alcohols (12 to 22 carbon atoms), with a melting point between 40 and 74° C.; iii) a second coating layer over the first one, which is constituted by microcrystalline waxes, paraffin waxes, vegetable waxes and synthetic waxes with a melting point between 80 and 100° C.

WO 2008015203 A2 describes microparticles or granules having a size between 0.1 and 5000 microns and intended for use in the zootechnical field and/or more generally in the veterinary field, constituted by a core which contains one or more substances having a pharmacological action, food supplements or diagnostic media, said substance or substances being characterized by the presence, within their chemical structure, of a cationic function or of an anionic function or of a function which is neutral but can be easily ionized in order to obtain a net charge, intimately mixed or adsorbed with a hydrated silicate of magnesium, aluminum, calcium and sodium, which is capable of absorbing water and causing reversible swelling; said core is coated by a double fatty layer constituted by two fats or waxes, in which the one having the highest melting point constitutes the inner layer (in contact with the core) while the one having the lowest melting point is arranged so as to form the outer layer.

SUMMARY OF THE INVENTION

The invention enables the controlled release of active ingredients in the gastrointestinal tract of animals, particularly ruminants. The technology and formulations described are capable of controlling the release of one or more substances which have a pharmacological action or play a role as feed supplements. In such compositions, the substance or substances carried by the micro particles are protected against the degradation that can occur in the first part of the digestive tract, in particular in the rumen, and can instead be released and absorbed in the intestine.

The present invention, in one embodiment, is a composition in form of micro particles with a content of active ingredients of at least 30%. The present invention, in another embodiment, is a composition in the form of microcapsules with a modified release of the active ingredients; in particular the release after a 24-hours dissolution test is less than 30% of the content of the actives.

DESCRIPTION OF THE INVENTION

The methods and compositions of the present invention relate to a system for the controlled release of one or more physiologically or pharmacologically active substances, in the form of micro particles having a size between 0.1 and 5000 microns and intended for use in the zootechnical field and/or the veterinary field. The compositions contain a core which comprises one or more substances having a pharmacological action or playing a role as a feed supplement (hereinafter referred to as active ingredient) and one or more carboxylic acids and/or their salts and eventually one or more excipients. Said core is coated by an outer layer of fats or waxes, and preferably by a mixture of glyceride of fatty acids.

Said active ingredient or ingredients are characterized by the presence of an amine functional group within their chemical structure, or more generally contain a functional group with basic characteristics; the core contains also one or more carboxylic acids and/or their salts, characterized by the presence of an acidic functional group within their chemical structure, intimately mixed in the core itself or added on its surface. These carboxylic acids or salts are characterized by the presence of at least one carboxyl group and a lipophilic functional group: the acidic function interacts with the basic function of the active ingredient and the lipophilic functional group helps to increase the lipophilicity of the core favoring the adhesion of the outer fat layer with the core itself.

Examples of active ingredients with a basic functional group suitable for the purpose cited above include, but are not limited to: isoleucine, leucine, lysine, methionine, phenylalanine, threonine, tryptophan, valine, alanine, asparagine, aspartic acid, cysteine, glutamic acid, glutamine, glycine, proline, selenocysteine, serine, tyrosine, arginine, histidine, choline, betaine, carnitine, thiamine, pyridoxine, streptomycin, colistin, tiamulin, neomycin, arginine, glucosamine, niacinamide and their salts, particularly choline chloride, betaine hydrochloride, lysine hydrochloride, thiamine hydrochloride, thiamine mononitrate, pyridoxine hydrochloride, colistin sulfate, and tiamulin fumarate. Examples of carboxylic acid with an acidic functional group suitable for the purpose cited above include but are not limited to: medium to long chain saturated and unsaturated fatty acids and their salts like mystiric, lauric, palmitic, stearic, oleic arachidic acids and their salts, aromatic carboxylic acids like benzoic acid and its salts, dicarboxylic acids like adipic, sebacic acids and their salts.

It is optionally possible to add excipients to the core of the microparticles according to the present invention. These excipients are capable of improving the formation of the core and can also contain a basic function in their chemical structure. Examples of excipients suitable for the purpose cited above include but are not limited to, are: clay, cob meal, silica, silicates, microcrystalline cellulose, polyvinylpyrrolidone, calcium phosphate, starch, alginate, amino modified silica, amino modified clays, amino modified cellulose, acrylic polymers with amine groups, chitosan, and gelatin. These excipients are typically used in an amount comprised between 0 and 40% of the total weight of the core.

Said core is coated by an outer layer of fats or waxes, and preferably by a mixture of glyceride of fatty acids. The ability to control release effectively is determined by the synergistic action of two phenomena: an interaction between the basic function and the carboxyl group in the core, and the barrier effect of the outer fat layer.

The controlled-release system according to the present invention is provided by preparing micro particles with a method which is composed of the steps as described below.

A mixture is prepared which comprises the active ingredient or ingredients and the carboxylic acid or acids. The amount of active or actives is comprised between 30 and 100% and preferably between 50 and 100%, even more preferably between 60 and 100% of the weight of the mixture. The amount of the carboxylic acid or acids is comprised between 0 and 70%, and preferably between 0 and 50%, even more preferably between 0 and 40%. Mixing can be performed with conventional fixed- or rotating-body mixers, since the choice of the type of mixer is not particularly critical with respect to the intended result. Starting from said mixture, microgranules are formed with the techniques commonly described for processes for granulation or agglomeration in the pharmaceutical field and in the food or feed industry. Examples in this regard are described abundantly in specialist literature, such as for example in Pharmaceutical principles of solid dosage forms, J. T. Carstensen (Ed.) (1993), Technomic Publishing Co., Lancaster (USA), or Pharmaceutical Pellettization Technology I. Ghebre-Sellassie (Ed.) (1989), Marcel Dekker, New York (USA), or Principi di tecnologie farmaceutiche, P. Colombo et al. (Eds.) (2004), Casa Editrice Ambrosiana, Milan (Italy), and are represented for example by the processes of extrusion-spheronization, fluid-bed granulation, rotating plate granulation, high-speed granulation, wet granulation, melt granulation, melt extrusion, melt agglomeration.

As an alternative to the method described above, the powder of the core can be transformed into micro granules by spraying it or mixing it with an aqueous solution which contains the active ingredient or ingredients. In this case, the concentration of said solution is comprised between 0.05 and 0.95 g/ml and preferably between 0.2 and 0.8 g/ml. The amount of solution of active substance that is added is such that the amount of active ingredient is comprised between 0.1 and 50% by weight of the core and preferably between 0.5 and 40% by weight of the core, even more preferably between 1 and 30% by weight of the core.

In this case also, the method for producing the granules can be for example extrusion-spheronization, fluid-bed granulation, rotating plate granulation, high-speed granulation, wet granulation, melt granulation, melt extrusion and melt agglomeration.

As an alternative to the method described above, the carboxylic acid or acids can be added to the core by spraying it or them on the surface of the preformed microgranules. In this case also the amount of carboxylic acid or acids is comprised between 0 and 70%, and preferably between 0 and 50%, even more preferably between 0 and 40% by weight of the core. Said acid or acids can be applied to the surface of the cores prepared as described earlier, after melting said acid or acids, by means of a so-called fluid bed or spray congealing technique or by drum mixer coating or in any case with a coating method such as those shown for example in the monograph Coated pharmaceutical dosage forms. Fundamentals, manufacturing techniques, biopharmaceutical aspects, test methods and raw materials, K. H. Bauer, K. Lehmann, H. P. Hosterwald, G. Rothgang (Edts), CRC Press, Boca Raton 1998.

It is optionally possible to add to the core, excipients which are capable of improving the formation of micro granules, in an amount comprised between 0 and 40% of the weight of the core and preferably between 0 and 30%. These excipients can be added to the core as powder or solubilized into aqueous solution.

In case the active ingredient is available in its pure (>96%) form as a granulate there may be no excipient needed to e.g. absorb a liquid product. In that case the preferred concentration of the excipients used for the production of the core is between 0 and 20%

In all the production methods described above, once the granules or microgranules have been obtained, they are dried if necessary with a drying method which uses a static or dynamic bed.

The cores thus obtained are coated with a layer of oils, fats or waxes, and preferably by a mixture of glyceride of fatty acids with a melting point comprised between 50 and 80° C. and preferably between 55 and 62° C. The fat is constituted preferably by mixtures of hydrogenated fatty acid glycerides. In particular, the preferred conditions provide for a C-16 fatty acid triglyceride content comprised between 40 and 70% and C-18 between 30 and 50% of the total fatty acid content.

The moisture content of the active ingredients and cores can not only impact storage of raw materials and finished goods, but also mixing ratios. Moisture content can also negatively impact viscosity due to the interaction of lysine and a preferred hydrogenated vegetable oil during the initial mixing process. The hygroscopic nature of lysine has been clearly demonstrated. Increased moisture will negatively impact matrix formation, manufacture via condensation and potentially finished goods performance/stability. The potential for moisture adsorption of the raw material supports the need for climate controlled storage conditions for the in-process raw lysine and selection of proper storage materials and procedures during receipt and handling of the raw material inventory.

Said fat can be applied to the surface of the cores prepared as described earlier, after melting said fat, by means of a so-called fluid bed or spray congealing technique or by drum mixer coating or in any case with a coating method such as those shown for example in the monograph Coated pharmaceutical dosage forms. Fundamentals, manufacturing techniques, biopharmaceutical aspects, test methods and raw materials, K. H. Bauer, K. Lehmann, H. P. Hosterwald, G. Rothgang (Edts), CRC Press, Boca Raton 1998.

The total amount of said coating fat applied is between 10 and 60% and preferably between 15 and 50% of the final weight of the micro particles.

It is optionally possible to add to the coating fat, excipients which are capable of improving their physical properties such as water resistance, viscosity, plasticity, adhesiveness, stress and temperature stability.

Examples of excipients capable of improving the physical properties of fat include but are not limited to lecithin, clay, silica, terpenes, sterols, calcium and sodium salts.

A particular characteristic of the present invention is that the ability to control the release effectively, and consequently reduce the rumen degradation, of active substances is determined by the synergistic action of two phenomena: an interaction between the basic function of the active and the acidic function of the carboxylic acid contained in the core; and the barrier effect of the coating fat layer. The interaction between the basic and acidic functions helps to slowing down the release of the active. This ability to control the release is verified with a 24 hours water dissolution test performed with an USP paddle apparatus (Apparatus 2) at 100 rpm and 38° C., the release after a 24-hours dissolution test is less than 30% of the content of the actives.

By way of non-limiting demonstration, examples related to the preparations and characteristics of the invention are cited hereafter.

Example 1

Controlled-Release Formulation Based on a Core that Contains Active Ingredients and Carboxylic Acid Intimately Mixed in it Composition:

| Core | Active ingredient | L-Lysine monohydrochloride (ADM, Decatur Illinois, USA) | 12.6 kg |
| --- | --- | --- | --- |
| | | L-Lysine in aqueous solution at 50% (ADM, Decatur Illinois, USA) | 2 kg |
| | Carboxylic acid | Stearic acid (BBC srl, Torre Boldone BG, IT) | 2 kg |
| Coating layer | Fat | Vegetoil S, hydrogenated vegetable oil (BBC srl, Torre Boldone BG, IT) | 4.4 kg |

The dry L-lysine monohydrochloride was mixed with liquid basic L-Lysine and stearic acid at 70° C. in a ploughshare mixer for 30 minutes. The core was then cooled to 40° C. and the coating layer was applied at 65° C. by spraying it in a pan coater. The microparticles were then cooled under 45° C.

A release dissolution test was performed with a USP paddle apparatus (Apparatus 2) at 38° C. and 100 r.p.m, in 700 ml of distilled water.

After 24 hours the released L-lysine was 18.7% with a standard deviation of 0.8.

Example 2

Controlled-Release Formulation Based on a Core that Contains Active Ingredients and Carboxylic Acid Added on their Surface Composition:

| Core | Active ingredients | L-Lysine monohydrochloride (ADM, Decatur Illinois, USA) | 240.38 kg |
| --- | --- | --- | --- |
| | | L-Lysine in aqueous solution at 50% (ADM, Decatur Illinois, USA) | 9.62 kg |
| | Carboxylic acid | Stearic acid (BBC srl, Torre Boldone BG, IT) | 44.6 kg |
| Coating layer | | Vegetoil S, hydrogenated vegetable oil (BBC srl, Torre Boldone BG, IT) | 62.4 kg |

The dry L-lysine monohydrochloride was mixed with liquid basic L-Lysine at 45° C. in a ribbon blender. The liquid was sprayed on the dry L-lysine monohydrochloride using a spraying nozzle at 2 barr pressure over a time of 5 minutes. The granules were then dried in a fluid bed. Stearic acid at 70° C. was added to the surface of the preformed microgranules by spraying it in a pan coater. The core was then cooled to 40° C. and the coating layer was applied at 65° C. by spraying it in a pan coater. The microparticles were then cooled under 45° C.

A release dissolution test was performed with a USP paddle apparatus (Apparatus 2) at 38° C. and 100 r.p.m, in 700 ml of distilled water.

After 24 hours the released L-lysine was 6.0% with a standard deviation of 0.6.

Example 3

Use of an Excipient in the Coating Layer

Composition:

| Core | Active ingredients | L-Lysine monohydrochloride (ADM, Decatur IL, USA) | 6523.8 g |
| --- | --- | --- | --- |
| | | L-Lysine in aqueous solution at 50% (ADM, Decatur, IL, USA) | 476.2 g |
| | Carboxylic acid | Stearic acid (BBC srl, Torre Boldone BG, IT) | 1000 g |
| coating layer | fat | Vegetoil S, hydrogenated vegetable oil (BBC srl, Torre Boldone BG, IT) | 1980 g |
| | excipient | Soy lecithin | 20 g |

The dry L-lysine monohydrochloride was mixed with liquid L-lysine at 45° C. in a rotary granulating machine. The granules were then dried in a fluid bed. Stearic acid at 70° C. was added to the preformed microgranules by spraying it in a pan coater. The core was then cooled at 40° C. and coated at 65° C. with the liquid fat containing the lecithin. The microparticles were then cooled under 45° C.

A release dissolution test was performed with a USP paddle apparatus (Apparatus 2) at 38° C. and 100 r.p.m, in 700 ml of distilled water.

After 24 hours the released L-lysine was 13.8% with a standard deviation of 0.4.

Comparative Example 4

Formulation without the Carboxylic Acid in the Core

In order to demonstrate the importance of the interaction between the basic function of the active with the carboxylic acid a formulation without the carboxylic acid and with the coating fat layer only was also produced and tested for release of the active ingredient. Composition:

| Core | Active ingredients | L-Lysine monohydrochloride (ADM, Decatur Illinois, USA) | 7810 g |
| --- | --- | --- | --- |
| Coating layer | fat | Vegetoil PH, hydrogenated vegetable oil (BBC srl, Torre Boldone BG, IT) | 3190 g |

The dry L-lysine monohydrochloride was coated with liquid hydrogenated vegetable oil 70° C. This was accomplished in a pan coater. The micro particles were than cooled under 45° C.

A release dissolution test was performed with an USP paddle apparatus at 38° C. and 100 r.p.m, in 700 ml of distilled water.

After 24 hours the released L-lysine was 80%.

Example 5

Controlled-Release Formulation Based on a Core that Contains Active Ingredient and Carboxylic Acid Salt Intimately Mixed in it Composition:

| Core | Active ingredient and carboxylic acids salt | Taminizer ® C (Taminco N.V., Gent, Belgium) | 210 kg |
|---|---|---|---|
| Coating layer | fat | Vegetoil S, hydrogenated vegetable oil (BBC srl, Torre boldone BG, IT) | 199 kg |
| | excipient | Soy lecithin | 1 kg |

Taminizer® C is a commercial brand product made according to patent WO2010072842 A1 and containing choline chloride and at least one salt of medium to long chain fatty acid. Taminizer® C was used as a core and it was coated at 65° C. with the liquid fat, containing the lecithin, by spraying it in a pan coater. The microparticles were then cooled under 45° C.

A release dissolution test was performed with a USP paddle apparatus (Apparatus 2) at 38° C. and 100 r.p.m, in 700 ml of distilled water.

After 24 hours the released choline chloride was 12.9% with a standard deviation of 0.6.

Example 6

Controlled-Release Formulation Based on a Core that Contains an Excipient at Very Low Concentration Composition:

| Core | Active ingredient | DL-methionine (Sumitomo Chemical, Tokyo, Japan) | 9730 g |
|---|---|---|---|
| | excipient | Starch licatab M (Roquette, Freres 62136 Lestrem France) | 270 g |
| | water | FU distilled water ACEF spa (Fiorenzuola, PC, IT) | 675 ml |
| | Carboxylic acid | Stearic acid (BBC srl, Torre Boldone BG, IT) | 1785 g |
| coating layer | fat | Vegetoil S, hydrogenated vegetable oil (BBC srl, Torre Boldone BG, IT) | 2500 g |

The dry DL-methionine was mixed with starch and water in the chamber of a rotary granulating machine. The granules were then dried in a fluid bed. Afterwards the stearic acid at 70° C. was added to the preformed microgranules by spraying it in a pan coater. The core was then cooled to 40° C. and the coating layer was applied at 65° C. The microparticles were then cooled under 45° C.

A release dissolution test was performed with an USP paddle apparatus (Apparatus 2) at 38° C. and 100 r.p.m, in 700 ml of distilled water.

After 24 hours the released DL-methionine was 11.4% with a standard deviation of 1.2.

Example 7

Controlled-Release Formulation Based on a Core that Contains an Excipient at High Concentration Composition:

| Core | Active ingredient and excipient | Choline Chloride 70% on cereal carrier (Balchem Corporation, NY, USA) | 4000 g |
|---|---|---|---|
| | | L-lysine in aqueous solution at 50% (ADM, Decatur Illinois, USA) | 143 |
| | carboxylic acid | Stearic acid (BBC srl, Torre Boldone BG, IT) | 857 g |
| coating layer | fat | Vegetoil S, hydrogenated vegetable oil (BBC srl, Torre Boldone BG, IT) | 3489.5 g |
| | excipient | Soy lechitin | 10.5 g |

Choline Chloride 70% is a dry commercial product containing choline chloride on a cereal carrier. It was mixed with liquid basic L-Lysine and stearic acid at 70° C. in a ploughshare mixer for 30 minutes. The core was then cooled to 40° C. and the coating layer was applied at 65° C. by spraying it in a pan coater. The microparticles were then cooled under 45° C.

A release dissolution test was performed with an USP paddle apparatus (Apparatus 2) at 38° C. and 100 r.p.m, in 700 ml of distilled water.

After 24 hours the released choline chloride was 4.0% with a standard deviation of 2.1.

Example 8

Release of Products in a Rumen Model

An in vitro rumen by-pass model was used to evaluate the by-pass rate. This model has shown to yield results that correlate well with action by-pass observed in ruminants.

This method follows the procedure described by Goering and Van Soest (Goering, H. K. and P. J. Van Soest. 1970. Forage fiber analysis. Agric. Handbook 379. ARS, USDA, Washington, D.C.) with some modifications on both preparation of rumen inocula and incubation media as described by Bossen (Bossen, D., D. R. Mertens, and M. R. Weisbjerg. 2008. Influence of Fermentation Methods on Neutral Detergent Fiber Degradation Parameters. Journal of Dairy Science. 91:1464). Extracted rumen is not strained but is used in the condition it was collected. This procedure enables rumen fluid to be delivered to the incubation vessels within 20 minutes of extraction from each donor animal in order to limit the negative effects on ruminal protozoa. A portion of the natural fiber mat is included in the extract to help maintain the integrity of the natural population of fiber-degrading micro-organisms.

The rumen by-pass rate has been evaluated for a methionine product that is prepared by conventional fat encapsulation which is typically done using spray cooling or spray freezing. The maximum inclusion rate for lysine in the hydrogenated vegetable oil matrix for such type of rumen protected methionine is about 50%.

The by-pass rate was evaluated over a period of 12 hours. A by-pass rate of 64% was observed in the model system.

In these experiments also the rumen by-pass rate has been evaluated for a 70% methionine product that has been prepared according to the method described in example 1. A by-pass rate of 98% was observed in the rumen by-pass model.

Figure 1:
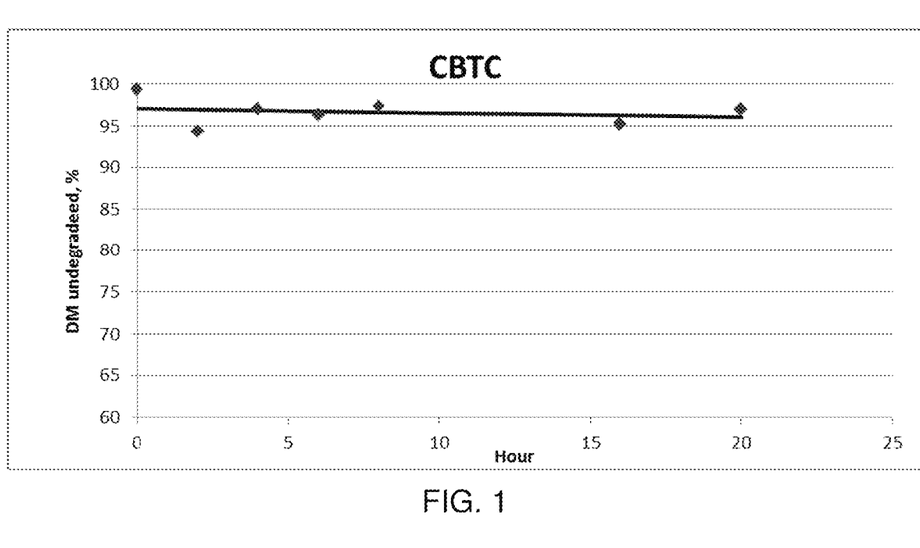
FIG. 1 is a chart of the level of protected choline named CBTC released over baseline from 0-20 hours following a meal
Figure 2:
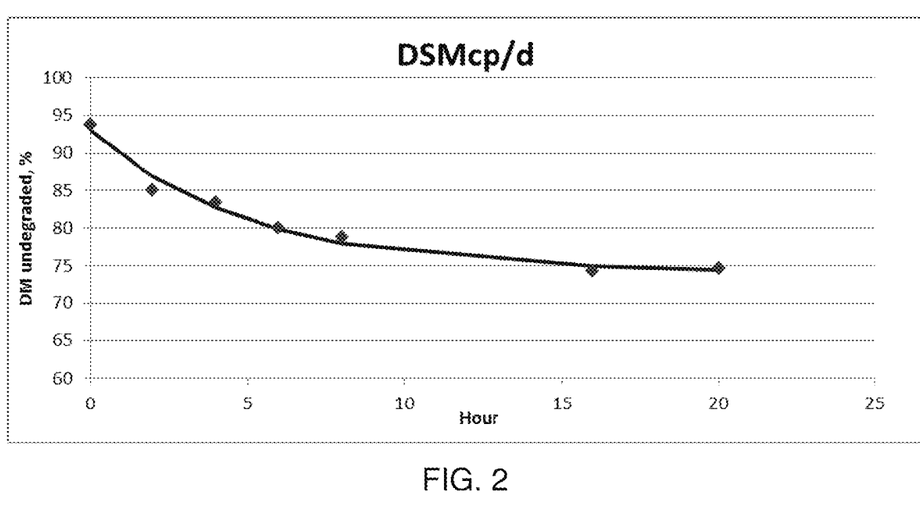
FIG. 2 is a chart of the level of protected choline named DSMcp/d released over baseline from 0-20 hours following a meal

A similar experiment was performed for a protected choline produced according to the method described in example 5 and labeled CBTC. The rumen by-pass rate can be compared with a choline product that is prepared by conventional fat encapsulation which is typically done using spray cooling or spray freezing. However these products typically have a lower concentration of the active ingredient due to increasing viscosity at higher levels of the active in the molten hydrogenated vegetable oil prior to spray freezing or spray cooling. The product evaluated in this experiment was prepared using the spray freezing technique and was labeled DSMcp/d. The results show that both products have a very significant rumen by-pass (FIGS. 1 and 2). The product prepared according to the method described in this invention has a superior rumen by-pass rate.

Example 9

Improvement of By-Pass Rates Evaluated in an In Vivo Ruminant Trial

Analysis of blood lysine levels after feeding different encapsulated lysine products to cows as well as free Lysine.HCl can be used to demonstrate why previous solutions fails to work for products containing a higher level of active ingredients. Three products have been compared. The first product is produced according to the method described in example 2 and labeled P1BT. The second product is produced according to the method described in example 1 and is labeled P2BT The following calculation was used to measure assess the impact of feeding 150 grams of lysine HCL (118 g lysine) per cow.

The zero hour baseline is subtracted from all points after zero hour for blood lysine measurements, to show the absolute increase in blood Lysine as measured in umol/l.

Figure 3:
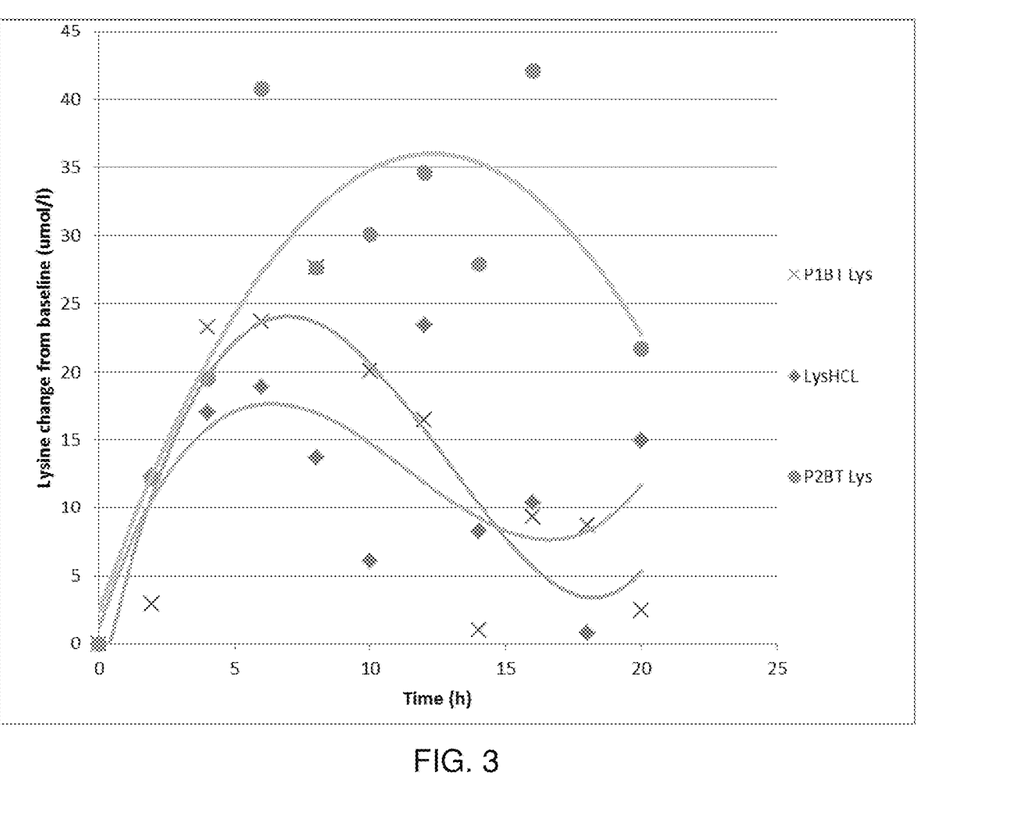
FIG. 3 is a chart of the level of lysine released over baseline from 0-20 hours following a meal for three products, P1BT (x) and P2BT (●), as compared to lysine HCl (♦).

The results show the superior bypass rate for the product described in the present invention. Both products P1BT and P2BT yield better plasma lysine levels than unprotected Lysine hydrochloride (FIG. 3). The overall area over the baseline represents the overall concentration increase of the active ingredient over the control animals during the 20 hours of the duration of the experiment The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclosure before them will be able to make modifications and variations therein without departing from the scope of the invention.

We claim:

1. Microparticles for the controlled release of one or more physiologically or pharmacologically active substances, comprising:
   a core comprising one or more active substances, said one or more active substances being selected from the group consisting of lysine, choline, and methionine, said one or more active substances being intimately mixed with one or more carboxylic acids and/or their salts, said one or more carboxylic acids being selected from the group consisting of lauric, palmitic, stearic, oleic, arachidic, benzoic, adipic, and sebacic;
   wherein the core exhibits controlled release of the one or more active substances such that less than 30% of the active substances are released within 24 hours; and
   a coating on the core comprising a mixture of hydrogenated fatty acid glycerides, and further providing that said hydrogenated fatty glycerides comprise a C-16 fatty acid triglyceride content of between 40 and 70% and a C-18 fatty acid triglyceride content of between 30 and 50% of the total fatty acid content, wherein the amount of the coating is between 10 and 60% of the final weight of the microparticles.

2. Microparticles as defined in claim 1, wherein the carboxylic acid is selected from the group consisting of medium and long chain saturated and unsaturated fatty acids and their salts consisting of laurine, palmitic, stearic, oleic arachidic acids, benzoic acids, and dicarboxylic acids consisting of adipic and sebacic acids.

3. Microparticles as defined in claim 1, wherein presence of said at least one lipophilic functional group improves the adhesion of the outer fat layer with the core.

4. Microparticles as defined in claim 1, wherein the core further comprises excipients.

5. Microparticles as defined in claim 4, wherein the excipient comprises a basic functional group.

6. Microparticles as defined in claim 4, wherein the excipients are selected from the group consisting of clay, cob meal, silica, microcrystalline cellulose, polyvinylpyrrolidone, calcium phosphate, calcium carbonate, magnesium oxide, starch, alginate, amino modified starches, amino modified silica, amino modified clays, amino modified cellulose, acrylic polymers with amine groups, chitosan, and gelatin.

7. Microparticles as defined in claim 4, wherein said excipients are present in an amount between 0.1 and 40% by weight.

8. Microparticles as defined in claim 1, wherein said active substances are present in an amount between 30 and 100% of the core.

9. Microparticles as defined in claim 1, wherein said carboxylic acids and/or their salts are present in an amount between 0.1 and 70%.

10. Microparticles as defined in claim 1, wherein said carboxylic acids and/or their salts are added to the core surface.

11. The microparticles of claim 1 whereby the active substances have an amine functional group.

12. The microparticles of claim 1, whereby the coating further comprises one or more excipients capable of improving physical properties of the coating.

13. The microparticles of claim 12 whereby the excipient is lecithin.

14. Microparticles according to claim 1 wherein the mixture of glyceride of fatty acids has a melting point comprised between 55 and 62° C.

* * * * *

UNITED STATES PATENT AND TRADEMARK OFFICE
CERTIFICATE OF CORRECTION

PATENT NO. : 11,110,057 B2
APPLICATION NO. : 13/081581
DATED : September 7, 2021
INVENTOR(S) : Marcello Arduini and Lauro Arduini It is certified that error appears in the above-identified patent and that said Letters Patent is hereby corrected as shown below:

On the Title Page

Item (75) Inventors:
Please change "Arduini Marcello" to --Marcello Arduini--
Please change "Arduini Lauro" to --Lauro Arduini--

Signed and Sealed this
Thirteenth Day of September, 2022

Katherine Kelly Vidal
*Director of the United States Patent and Trademark Office*